United States Patent [19]

Gaffar et al.

[11] Patent Number: 5,525,330
[45] Date of Patent: Jun. 11, 1996

[54] ANTIPLAQUE ANTIGINGIVITIS, ANTICARIES ORAL COMPOSITION

[75] Inventors: Abdul Gaffar, Princeton; John J. Afflitto, Brookside; Malcolm I. Williams, Piscataway, all of N.J.

[73] Assignee: Colgate Palmolive Company, New York, N.Y.

[21] Appl. No.: 343,408

[22] Filed: Nov. 22, 1994

Related U.S. Application Data

[60] Division of Ser. No. 103,005, Aug. 5, 1993, Pat. No. 5,368,844, which is a continuation-in-part of Ser. No. 992,416, Dec. 16, 1992, abandoned.

[51] Int. Cl.$^6$ .............................. A61K 7/16; A61K 7/18
[52] U.S. Cl. .............................. 424/52; 424/49; 424/54; 424/57
[58] Field of Search .......................... 424/49–58

[56] References Cited

U.S. PATENT DOCUMENTS

| | | | |
|---|---|---|---|
| 3,429,963 | 2/1969 | Shedlovsky | 424/56 |
| 3,629,477 | 12/1971 | Model et al. | 424/340 |
| 3,941,772 | 3/1976 | Ploser et al. | 260/239 |
| 3,956,480 | 5/1976 | Dichter et al. | 424/54 |
| 3,960,888 | 6/1976 | Ploser et al. | 260/326.5 |
| 3,988,318 | 10/1976 | Copes et al. | 260/239.3 R |
| 3,988,350 | 10/1976 | Copes et al. | 260/326.5 FL |
| 3,988,443 | 10/1976 | Ploser et al. | 424/200 |
| 4,022,880 | 5/1977 | Vinson et al. | 424/49 |
| 4,423,043 | 12/1983 | Lukas et al. | 424/229 |
| 4,504,228 | 3/1985 | Maetani et al. | 433/199 |
| 4,975,271 | 12/1990 | Dunn et al. | 424/49 |
| 4,987,148 | 1/1991 | Hidaka et al. | 514/441 |
| 5,037,637 | 8/1991 | Gaffar et al. | 424/52 |
| 5,077,049 | 12/1991 | Dunn et al. | 424/426 |
| 5,185,386 | 2/1993 | Cohen et al. | 523/105 |
| 5,279,816 | 1/1994 | Church et al. | 424/53 |
| 5,368,844 | 11/1994 | Gaffar et al. | 424/49 |

FOREIGN PATENT DOCUMENTS

| | | | |
|---|---|---|---|
| 38416 | 10/1981 | European Pat. Off. | A01N 25/02 |
| 539751 | 5/1993 | European Pat. Off. | A61K 9/00 |
| 597671 | 3/1978 | U.S.S.R. | C07C 103/78 |
| 9200718 | 1/1992 | WIPO | A61K 6/00 |

*Primary Examiner*—Shep K. Rose
*Attorney, Agent, or Firm*—Robert L. Stone; Murray M. Grill

[57] ABSTRACT

Oral composition containing an effective amount of N-methylpyrrolidone alone or in combination with a noncationic antibacterial agent such as Triclosan for topical application for the prevention of plaque, gingivitis and/or caries.

22 Claims, No Drawings

ANTIPLAQUE ANTIGINGIVITIS, ANTICARIES ORAL COMPOSITION

This is a division of Ser. No. 08/103,005 filed Aug. 5, 1993 now U.S. Pat. No. 5,368,844, granted Nov. 29, 1994, which is a continuation-in-part of Ser. No. 07/992,416, filed Dec. 16, 1992, now abandoned.

FIELD OF THE INVENTION

The present invention relates to an antiplaque, antigingivitis, anticaries oral composition. More particularly, the present invention relates to an oral composition containing N-methylpyrrolidone alone or in combination with a noncationic antibacterial compound.

BACKGROUND OF THE INVENTION

Oral compositions which inhibit calculus formation on dental surfaces are highly desirable since calculus is one of the causative factors in periodontal conditions. The reduction of calculus, therefore, promotes oral hygiene. Polyphosphates, such as tetraalkali metal pyrophosphates, are examples of anticalculus agents.

Dental plaque is a precursor of calculus. Unlike calculus, however, plaque may form on any part of the tooth surface, particularly at the gingival margin. Hence, besides being unsightly, it is implicated in the occurrence of gingivitis.

Accordingly, it is desirable to include effective antiplaque agents in oral compositions, optionally in combination with an anticalculus agent. Antiplaque agents found particularly effective are noncationic antibacterial agents, such as halogenated diphenyl ethers, especially Triclosan (2',4,4'-2-trichloro-2-hydroxydiphenyl ether), as disclosed in Gaffar et al., U.S. Pat. No. 5,037,637, incorporated herein by reference. However, since halogenated diphenyl ethers and other noncationic antibacterial agents are not readily soluble in water, alternate solvents are desirable to optimize their effectiveness.

Pyrrolidone compounds, other than N-methylpyrrolidone, have previously been employed for a variety of purposes in oral compositions. For example, Roberts et al., Reissue U.S. Pat. No. 29,634 discloses the use of polyvinyl pyrrolidone (PVP) as a binder to form a polishing agent into agglomerated particles. PVP is disclosed as a viscosity adjuster in Prussin, U.S. Pat. No. 3,954,962, as a gelling agent in Norfleet, U.S. Pat. No. 3,840,657, a cooling agent in Humbert et al., U.S. Pat. No. 3,917,613, and a synthetic gum in Aguilar U.S. Pat. No. 4,344,931. PVP is further disclosed for uses in other oral compositions with hydrogen peroxide. Both Simon et al, U.S. Patent Nos. 4,521,403 and 4,567,036 teach to the use of PVP with hydrogen peroxide in controlling disease of the teeth and periodontum. Merianos et al, U.S. Pat. No. 5,130,124 teaches to the use of PVP as a film forming antimicrobial composition when combined with hydrogen peroxide.

Pyrrolidone compounds have also been incorporated into dentifrice compositions to kill bacteria and/or retard the formation of plaque and tartar. Ploger et al., U.S. Pat. No. 3,960,888, disclose pyrrolidone-5,5-diphosphonic acids as antitartar and antiplaque agents. Murdrak, U.S. Pat. No. 2,757,125, discloses N-higher alkyl-4-carboxy-2-pyrrolidones as antibacterial agents for oral compositions. Login et al., U.S. Patent Nos. 4,732,990; 4,830,850; and 4,837,013 disclose quaternized nitrogen compounds including derivatives of pyrrolidone as antibacterial agents for dentifrice compositions and/or mouthwashes.

Substituted pyrrolidone compounds have been used to retard plaque formation as disclosed in Blackburne et al, U.S. Pat. No. 4,093,711; Shapiro et al., U.S. Pat. Nos. 4,117,107 and 4,117,108: and Hollister, U.S. Pat. No. 4,621,120.

Dunn et al. U.S. Pat. No. 4,975,271, teaches to use N-methylpyrrolidone as one of several skin penetration enhancer solvents for a drug or bioactive agent which is applied directly to oral mucosa. Dental surfaces are not contacted. Mouthrinses and other topically applied oral medicinal agents which would contact dental surfaces as well as oral mucosa are specifically excluded.

It would be desirable to enhance the solubility of noncationic antibacterial agents to improve their effectiveness. It would also be desirable to provide an oral composition containing an antiplaque agent with enhanced antiplaque effectiveness.

SUMMARY OF THE INVENTION

In accordance with the present invention N-methylpyrrolidone [1-methyl-2-pyrrolidone (1)] has been found to have a potent antiplaque effect when employed in an oral composition alone and to enhance the effect of noncationic antibacterial agents such as halogenated diphenyl ethers, particularly Triclosan in the prevention of plaque, gingivitis and caries.

The present invention is directed to an oral composition comprising an orally acceptable vehicle suitable for topically contacting dental surfaces and gums and up to about 20% by weight N-methylpyrrolidone as an antiplaque agent in the presence or absence of an antibacterial agent, preferably a substantially water-insoluble noncationic antibacterial agent.

The amount of N-methylpyrrolidone in this invention is typically about 0.5 to 20% by weight based on the total weight of the dental composition and preferably about 1 to 15% and most preferably about 5 to 10%. Gum irritation can be avoided when N-methylpyrrolidone is used in amounts of up to about 20% by weight of the topically applied oral composition.

A further aspect of the invention is a method for reducing plaque formation comprising topically contacting dental surfaces and gums with an oral composition coma,rising a liquid vehicle suitable for topically contacting dental surfaces and gums and as an antiplaque agent, up to about 20% N-methylpyrrolidone based on the total weight of the composition. Preferably, the composition is contacted with dental surfaces and gums about 1 to 3 times a day.

The composition and process may include one or more antibacterial agents which are particularly desirable from consideration of antiplaque effectiveness, safety and formulation.

DETAILED DESCRIPTION OF THE INVENTION

The following antibacterial agents may be incorporated into the oral composition of the present invention:

HALOGENATED DIPHENYL ETHERS

2',4,4'-trichloro-2-hydroxy-diphenyl ether (Triclosan)

2,2'-dihydroxy-5,5'-dibromo-diphenyl ether

PHENOLIC COMPOUNDS (including phenol and its homologs, mono- and poly-alkyl and aromatic halophenols, resorcinol and its derivatives and bisphenolic compounds and

| PHENOL AND ITS HOMOLOGS | |
|---|---|
| PHENOL | |
| 2 Methyl | Phenol |
| 3 Methyl | Phenol |
| 4 Methyl | Phenol |
| 4 Ethyl | Phenol |
| 2,4-Dimethyl | Phenol |
| 2,5-Dimethyl | Phenol |
| 3,4-Dimethyl | Phenol |
| 2,6-Dimethyl | Phenol |
| 4-n-Propyl | Phenol |
| 4-n-Butyl | Phenol |
| 4-n-Amyl | Phenol |
| 4-tert-Amyl | Phenol |
| 4-n-Hexyl | Phenol |
| 4-n-Heptyl | Phenol |

| MONO- AND POLY-ALKYL AND AROMATIC HALOPHENOLS | |
|---|---|
| Methyl | p-Chlorophenol |
| Ethyl | p-Chlorophenol |
| n-Propyl | p-Chlorophenol |
| n-Butyl | p-Chlorophenol |
| n-Amyl | p-Chlorophenol |
| sec.-Amyl | p-Chlorophenol |
| n-Hexyl | p-Chlorophenol |
| Cyclohexyl | p-Chlorophenol |
| n-Heptyl | p-Chlorophenol |
| n-Octyl | p-Chlorophenol |

| O-CHLOROPHENOL | |
|---|---|
| Methyl | o-Chlorophenol |
| Ethyl | o-Chlorophenol |
| n-Propyl | o-Chlorophenol |
| n-Butyl | o-Chlorophenol |
| n-Amyl | o-Chlorophenol |
| tert-Amyl | o-Chlorophenol |
| n-Hexyl | o-Chlorophenol |
| n-Heptyl | o-Chlorophenol |

| p-CHLOROPHENOL | |
|---|---|
| o-Benzyl | p-Chlorophenol |
| o-Benzyl-m-methyl | p-Chlorophenol |
| o-Benzyl-m, m-dimethyl | p-Chlorophenol |
| o-Phenylethyl | p-Chlorophenol |
| o-Phenylethyl-m-methyl | p-Chlorophenol |
| 3-Methyl | p-Chlorophenol |
| 3,5-Dimethyl | p-Chlorophenol |
| 6-Ethyl-3-methyl | p-Chlorophenol |
| 6-n-Propyl-3-methyl | p-Chlorophenol |
| 2-iso-Propyl-3-methyl | p-Chlorophenol |
| 2-Ethyl-3,5-dimethyl | p-Chlorophenol |
| 6-sec. Butyl-3-methyl | p-Chlorophenol |
| 2-iso-Propyl-3,5-dimethyl | p-Chlorophenol |
| 6-Diethylmethyl-3-methyl | p-Chlorophenol |
| 6-iso-Propyl-2-ethyl-3-methyl | p-Chlorophenol |
| 2-sec. Amyl-3,5-dimethyl | p-Chlorophenol |
| 2-Diethylmethyl-3,5-dimethyl | p-Chlorophenol |
| 6-sec. Octyl-3-methyl | p-Chlorophenol |

| p-BROMOPHENOL | |
|---|---|
| Methyl | p-Bromophenol |
| Ethyl | p-Bromophenol |
| n-Propyl | p-Bromophenol |
| n-Butyl | p-Bromophenol |
| n-Amyl | p-Bromophenol |
| sec-Amyl | p-Bromophenol |
| n-Hexyl | p-Bromophenol |
| cyclohexyl | p-Bromophenol |

| o-BROMOPHENOL | |
|---|---|
| tert.-Amyl | o-Bromophenol |
| n-Hexyl | o-Bromophenol |
| n-Propyl-m,m-Dimethyl | o-Bromophenol |

2-Phenyl Phenol
4-chloro-2-methyl phenol
4-chloro-3-methyl phenol
4-chloro-3,5-dimethyl phenol
2,4-dichloro-3,5-dimethyl phenol
3,4,5,6-terabromo-2-methyl phenol
5-methyl-2-pentylphenol
4-isopropyl-3-methylphenol
5-chloro-2-hydroxydiphenyl-methane

| RESORCINOL AND ITS DERIVATIVES | |
|---|---|
| RESORCINOL | |
| Methyl | Resorcinol |
| Ethyl | Resorcinol |
| n-propyl | Resorcinol |
| n-Butyl | Resorcinol |
| n-Amyl | Resorcinol |
| n-Hexyl | Resorcinol |
| n-Heptyl | Resorcinol |
| n-Octyl | Resorcinol |
| n-Nomyl | Resorcinol |
| Phenyl | Resorcinol |
| Benzyl | Resorcinol |
| Phenylethyl | Resorcinol |
| Phenylpropyl | Resorcinol |
| p-Chlorobenzyl | Resorcinol |
| 5-Chloro | 2,4-Dihydroxydiphenyl Methane |
| 4'-Chloro | 2,4-Dihydroxydiphenyl Methane |
| 5-Bromo | 2,4-Dihydroxydiphenyl Methane |
| 4'-Bromo | 2,4-Dihydroxydiphenyl Methane |

| BISPHENOLIC COMPOUNDS |
|---|
| 2,2'-methylene bis (4-chlorophenol) |
| 2,2'-methylene bis (3,4,6-trichlorophenol) |
| 2,2'-methylene bis (4-chloro-6-bromophenol) |
| bis (2-hydroxy-3,5-dichlorophenyl) sulfide |
| bis (2-hydroxy-5-chlorobenzyl) sulfide |

| HALOGENATED CARBANILIDES |
|---|
| 3,4,4'-trichlorcarbanilide |
| 3-trifluoromethyl-4,4'-dichlorocarbanilide |
| 3,3',4-trichlorocarbanilide |

The antibacterial agent, when employed, is present in the oral composition in an effective antiplaque amount, typically about 0.01 to 5% by weight, preferably about 0.03 to 1% by weight. The antibacterial agent is substantially water-insoluble, meaning that its solubility is less than about 1% by weight in water at 25° C. and may be even less than about 0.01% by weight. The solubility of the antibacterial agent is increased by the addition of an effective amount of n-methylpyrrolidone. As a consequence, a greater amount of the antibacterial agent is delivered to the teeth where plaque is likely to develop.

The preferred halogenated diphenyl ether is Triclosan. The preferred phenolic compounds are n-hexyl resorcinol and 2,2'-methylene bis (4-chloro-6-bromophenol). The most preferred antibacterial antiplaque compound is Triclosan. Triclosan is described in more detail in Gaffar et al., U.S. Pat. No. 5,037,637, and references cited therein, each of which is incorporated herein by reference.

Cationic antibacterial agents may optionally be employed in the compositions of the present invention. Such agents are disclosed in, for example, Gaffar, U.S. Pat. No. 4,339,430, incorporated herein by reference, and include antibacterial quaternary ammonium compounds such as benzethonium chloride and dissobutylphenoxyethoxyethyl dimethyl benzyl ammonium chloride.

Other antibacterial antiplaque quaternary ammonium compounds include those in which one or two of the substituents on the quaternary nitrogen has a carbon chain length (typically an alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, dodecyl dimethyl (2-phenoxyethyl) ammonium bromide, benzyl dimethyl stearyl ammonium chloride, cetylpyridinium chloride and quaternized 5-amino- 1,3-bis (2-ethylhexyl)-5-methyl hexa hydropyrimidine are exemplary of other typical quaternary ammonium antibacterial agents.

Other types of cationic antibacterial agents which are desirably incorporated in the present composition include the amidines such as substituted guanidines e.g. chlorhexidine and the corresponding compound, alexidine, having 2-ethylhexyl groups instead of chlorophenyl groups, as well as other known bisbiguanides.

Cationic tertiary amines may also be used and include those having one fatty alkyl group (typically 12 to 18 carbon atoms) and 2 poly(oxyethylene) groups attached to the nitrogen (typically containing a total of from 2 to 50 ethenoxy groups per molecule) and salts thereof with acids and compounds of the structure:

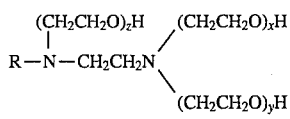

where R is a fatty alkyl group containing 12 to 18 carbon atoms and x, y, and z total 3 or higher, as well as salts thereof.

Cationic antibacterial agents which may be employed in the practice of this invention are typically employed in amounts such that the oral product contains about 0.001 to 15% by weight of the agent, preferably about 0.01 to 5% by weight, and most preferably about 0.25 to 1.0% by weight referring to its free base form, based on the total weight of the oral composition.

Other cationic antibacterial agents for use in the present invention are described in Gaffar, U.S. Pat. No. 4,339,430, and references mentioned therein.

The present oral composition preferably contains an anticalculus agent. The preferred anticalculus agents are linear molecularly dehydrated polyphosphate salts which are well known, being generally employed in the form of their wholly or partially neutralized water-soluble alkali metal (e.g. potassium and preferably sodium) or ammonium salts, and any mixtures thereof. Representative examples include sodium hexametaphosphate, sodium tripolyphosphate, disodium diacid, trisodium monoacid and tetrasodium pyrophosphates and the like. The anticalculus agents are generally employed in the instant oral compositions in approximate amounts of about 0. 1 to 7% by weight, more preferably about 2 to 7% by weight.

Particularly desirable anticalculus agents of the polyphosphate type are tetraalkali metal pyrophosphates, including mixtures thereof, such as tetrasodium pyrophosphate, tetrapotassium pyrophosphate and mixtures thereof. An anticalculus agent comprising about 4.3% to 7% by weight of the oral compositions wherein the weight ratio of tetrapotassium pyrophosphate to tetrasodium pyrophosphate is from about 4.3:2.7 to about 6:1 is especially preferred.

In order to optimize the effectiveness of the oral composition, if one or more polyphosphate compounds are present, inhibitors against enzymatic hydrolysis of the polyphosphate are desirably present. Such inhibitors include a fluoride ion source or synthetic anionic polymeric polycarboxylates.

The sources of fluoride ions, or fluorine-providing component, as well as the acid phosphatase and pyrophosphatase enzyme inhibitor component, are well known in the art as anti-caries agents. These compounds may be slightly soluble in water or may be fully water-soluble. They are characterized by their ability to release fluoride ions in water, by their freedom from undesired reaction with other compounds of the oral preparation and by their anticaries and enzyme inhibitory activity. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type or oral preparation, but it must be a non-toxic amount, generally about 0.005 to about 3.0% in the preparation. In a dentifrice preparation, e.g. dental gel, toothpaste (including cream), tooth powder, or dental tablet, an amount of such compound which releases up to about 5,000 ppm of fluoride ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1 to 3%, more typically about 0.76%.

In dentifrice preparations such as lozenges and chewing gum, the fluorine-providing compound is typically present in an mount sufficient to release up to about 500 ppm, preferably about 25 to 300 ppm by weight of fluoride ion. Generally about 0.005 to 1.0% by weight of such compound is present.

Synthetic anionic polymeric polycarboxylates useful as enzyme inhibitors, particularly to inhibit alkaline phosphatase, may optionally enhance the antibacterial effect of the substantially water-insoluble noncationic antibacterial agents such as Triclosan. Examples of these agents are disclosed in Shedlovsky U.S. Pat. No. 3,429,963, Dichter et al. U.S. Pat. No. 3,956,480, Gaffar U.S. Patent Nos. 4,138, 477 and 4,152,420, and Gaffar et al. U.S. Pat. No. 4,183,914, each incorporated herein by reference.

The synthetic anionic polymeric polycarboxylates optionally but preferably employed herein are, as indicated above, well known, being often employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to 1,000,000. These copolymers are available for example as Gantrez AN 139 (M.W. 500,000), AN 119 (M.W. 250,000); and preferably S-97 Pharmaceutical Grade of GAF Corporation. The term "synthetic" is intended to exclude known thickening or gelling agents comprising carboxymethylcellulose and other derivatives of cellulose and natural gums.

Other operative polymeric polycarboxylates include those disclosed in Dichter et al., U.S. Pat. No. 3,956,480, referred to above, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to Gaffar, U.S. Pat. No. 4,138,477, and Gaffar et al., U.S. Pat. No. 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinyl acetate, vinyl chloride, dimethyl maleate and the like. Copolymers contain sufficient carboxylic salt groups for water-solubility.

Also useful herein are so-called carboxyvinyl polymers disclosed as toothpaste components in Chown et al. U.S. Pat. No. 3,980,767; Roberts et al. U.S. Pat. No. 3,935,306; Perla et al. U.S. Pat. No. 3,919,409; Harrison U.S. Pat. No. 3,911,104, and Colodney et al. U.S. Pat. No. 3,711,604. They are commercially available for example under the trademarks Carbopol 934, 940 and 941 of B. F. Goodrich, these products consisting essentially of a colloidally water-soluble polymer of polyacrylic acid cross-linked with from about 0.75% to 2.0% by weight of polyallyl sucrose or polyallyl pentaerythritol as cross-linking agent.

The synthetic anionic polymeric polycarboxylate component is mainly a hydrocarbon with optional halogen and O-containing substituents and linkages as present in for example ester, ether and OH groups, and when present is generally employed in the instant compositions in approximate weight amounts of about 0.05 to 3% by weight, preferably about 0.05 to 2% by weight, more typically employed in dentifrice compositions typically containing a dental abrasive and used in conjunction with brushing of the teeth, e.g. tooth pastes (including creams), gels, powders and tablets. Amounts in excess of these ranges may be employed for thickening or gelling purposes. The preferred synthetic anionic polymeric carboxylates (e.g. Gantrez) also enhance the antibacterial effect of the antiplaque agent. Other antibacterial-enhancing agents may also be used.

Antibacterial-enhancing agents (AEAs), when present, enhance delivery of the water-insoluble noncationic antibacterial agent to, and retention thereof on, oral surfaces, in accordance with a preferred embodiment of the present invention. AEAs are employed in amounts effective to achieve such enhancement preferably within the range in the oral composition of about 0.005% to 4%, preferably about 0.1% to 3%, more preferably about 0.5% to 2.5% by weight.

The AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water-insoluble or preferably water (saliva) soluble or swellable (hydratable, hydrogel forming). It preferably has a (weight) average molecular weight of about 100 to 1,000,000, preferably about 1,000 to 1,000,000, more preferably about 2,000 or 2,500 to 250,000 or 500,000.

The AEA ordinarily contains at least one delivery-enhancing group, which is preferably acidic such as sulfonic, phosphonic, or more preferably phosphonic or carboxylic, or salt thereof, e.g. alkali metal or ammonium, and at least one organic retention-enhancing group, preferably a plurality of both the delivery enhancing and retention-enhancing groups, which latter groups preferably have the formula $—(X)_n—R$ wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives" are intended to include substituents on R which are generally nonhydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such retention-enhancing groups limed in Table 1.

TABLE 1

| n | X | $-(X)_nR$ |
|---|---|---|
| 0 | — | methyl, ethyl, propyl, butyl, isobutyl, t-butyl cyclohexyl, allyl, benzyl, phenyl, chlorophenyl, xylyl, pryridyl, furanyl, acetyl, benzoyl, butyryl, terephthaloyl, etc. |
| 1 | O | ethoxy, benzyloxy, thioacetoxy, phenoxy, carboethoxy, carbobenzyloxy, etc. |
|   | N | ethylamino, diethylamino, propylamido, benzylamino, benzoylamido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | $SO_2$ | butylsulfonyl, allylsulfonyl, benzylsulfonyl, phenylsulfonyl, etc. |
|   | P | diethylphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzylphosphinoxy, methylphenylphosphinoxy, etc. |
|   | Si | trimethylsilyl, dimethylbutylsilyl, dimethylbenzylsilyl, dimethylvinylsilyl, dimethylallylsilyl, etc. |

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is a anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEAs disclosed herein which do not contain both delivery-enhancing groups and retention enhancing groups may and preferably should be chemically modified in known manner to obtain the preferred AEAs containing both such groups and preferably a plurality of each such groups. In the case of the preferred polymeric AEAs, it is desirable, for maximizing substantivity and delivery of the antibacterial agent to oral surfaces, that the repeating units in the polymer chain or backbone containing the acidic delivery-enhancing groups constitute at least about 10%, preferably at least about 50%, more preferably at least about 80% up to 95% or 100% by weight of the polymer.

According to a preferred embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of Formula I:

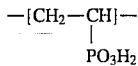

which however does not contain a retention-enhancing group. A group of the latter type would however be present in poly(1-phosphonopropene) with units of Formula II:

$$-[CH-CH]- \quad \quad (II)$$
$$\phantom{-[}|\phantom{CH}| $$
$$\phantom{-[}CH_3 \phantom{C}PO_3H_2$$

A preferred phosphonic acid-containing AEA for use herein is poly (beta styrene phosphonic acid) containing units of Formula III:

$$-[CH-CH]- \quad \quad (III)$$
$$\phantom{-[}|\phantom{CH}| $$
$$\phantom{-[}Ph \phantom{C}PO_3H_2$$

wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of Formula III alternating or in random association with units of Formula I above, or poly (alpha styrene phosphonic acid) containing units of Formula IV:

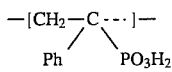

in which the delivery-enhancing and retention-enhancing groups are geminally bonded to the chain.

These styrene phosphonic acid polymers and their copolymers with other inert ethylenically unsaturated monomers generally have molecular weights in the range of about 2,000 to 30,000, preferably about 2,500 to 10,000. Such "inert" monomers do not significantly interfere with the intended function of any copolymer employed as an AEA herein.

Other phosphonic-containing polymers include, for example, phosphonated ethylene having units of the Formula V:

where n may for example be an integer or have a value giving the polymer a molecular weight of about 3,000; and sodium poly(butene-4,4-diphosphonate) having units of the Formula VI:

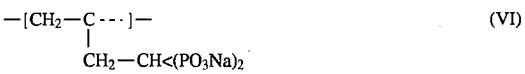

and poly (allyl bis (phosphonoethyl amine) having units of Formula VII:

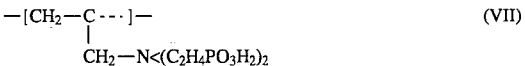

Other phosphonated polymers, for example poly (allyl phosphono acetate), phosphonated polymethacrylate, etc. and the geminal diphosphonate polymers disclosed in EP Publication 0321233 may be employed herein as AEAs, provided of course that they contain or are modified to contain the above-defined organic retention-enhancing groups. As previously indicated, the most preferred AEAs are synthetic anionic polymeric carboxylates.

The pH of the dentifrice preparations of this invention is generally in the range of from about 4.5 to about 10 and typically from about 5.5 to 9. The pH is preferably in the range of from about 6 to about 8.0. It is noteworthy that the compositions of the invention may be applied orally at said pH ranges without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In certain desirable forms of this invention, the dentifrice composition may be substantially solid or pasty in character, such as tooth powder, a dental tablet, a tooth paste (cream), or a dental gel. The vehicle of such solid or pasty dentifrice preparations typically contains an orally or dentally acceptable polishing material for use in conjunction with a brushing of the teeth. Examples of such polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 4,070,510 such as melamine-, phenolic-, and urea-formaldehydes, and cross-linked polyepoxides and polyesters. Preferred polishing materials include silica gel or colloidal silica, and complex amorphous alkali metal alumino-silicates.

When visually clear gels are desired, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any conventional manner. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in concentrations of about 10% to 99% by weight. Preferably, it is present in amounts ranging from about 10% to 75% by weight in toothpaste or gel and from about 70% to 99% by weight in tooth powder or tablet.

In a toothpaste, the topical liquid vehicle may comprise water and humectant typically in an amount ranging from about 10% to 90% by weight of the preparation. Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration, about 3 to 30% by weight of water, about 0 to 80% by weight of glycerine, and about 20 to 80% by weight of sorbitol is preferably employed.

Toothpastes (creams) and gels typically contain in the topical vehicle a natural or synthetic thickener or gelling agent in proportions of about 0.1 to 10, preferably about 0.5 to 5% by weight. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% $MgO$, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitably labeled packages. Thus, a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

In the aspect of the present invention wherein the oral composition is a mouthwash or liquid dentifrice, substantially liquid in character, the topical vehicle, particularly in a mouthwash, is typically a water-alcohol mixture. Generally, the weight ratio of water to alcohol is in the range of from about 1:1 to 20:1, preferably about 3:1 to 10:1 and more preferably about 4:1 to 6:1. The total amount of the water-alcohol mixture in this type of preparation is typically in the range of from about 70 to 99.9% by weight. The alcohol is a non-toxic alcohol such as ethanol or isopropanol, most preferably ethanol. The alcohol is believed to assist in dissolving water-insoluble noncationic antibacterial agents. Flavoring oil is also believed to perform the same function. Humectant such as glycerine and sorbitol may be present in an mount of about 10 to 30% by weight. Liquid dentifrices typically contain about 50 to 85% of water, may contain about 0.5 to 20% by weight of nontoxic alcohol and may also contain about 10 to 40% by weight of humectant such as glycerine and/or sorbitol. Reference here to sorbitol refers to the material typically available commercially in 70% aqueous solutions.

As indicated, the noncationic antibacterial agent is substantially water-insoluble. However, in the present invention, particularly with the AEA, such as polycarboxylate, present in the mouthwash or liquid dentifrice, organic surface-active agent, flavoring oil or non-toxic alcohol are believed to aid dissolving the antibacterial agent to assist it to reach soft oral tissue at or near the gums as wall as tooth surfaces. Organic surface-active agents and/or flavoring oils may also assist dissolving the antibacterial agents as optional ingredients in oral dentifrice compositions.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl awl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolmine salts of N-lauroyl, N-myristoyl, or N-palmitoyl sarcosine which should be substantially free from soap or similar higher fatty acid material as well as N-methyl-N-cocoyl (or oleoyl or palmitoyl) taurines, The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anti-calculus agents, and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with the active components of the instant invention are to be avoided.

Any suitable flavoring or sweetening material may also be employed. Examples of suitable flavoring constituents are flavoring oils, e.g. oil of spearmint; peppermint, wintergreen, sassafras, clove, sage, eucalyptus, marjoram, cinnamon, lemon, and orange, and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like. Suitably, flavoring and sweetening agents may together comprise from about 0.1% to 5% by weight or more of the preparation.

In the preferred practice of this invention an oral composition according to this invention such as a dentifrice is preferably applied as by brushing regularly to dental enamel, such as every second or third day or preferably from 1 to 3 times daily, at a pH of about 4.5 to 10, generally about 5.5 to 9, preferably about 6 to 8, for at least 2 weeks up to 8 weeks or more up to lifetime. The dentifrice is typically removed by rinsing with water after each application.

The compositions of this invention can be incorporated in lozenges, or in chewing gum or other products, e.g. by stirring into a warm gum base topical vehicle or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The topical vehicle or carrier in a tablet or lozenge is a non-cariogenic solid water-soluble polyhydric alcohol (polyol) such as mannitol, xylitol, sorbitol, malitol, a hydrogenated starch hydrolysate, Lycasin, hydrogenated glucose, hydrogenated disaccharides, and hydrogenated polysaccharides, in an amount of about 90 to 98% by weight of the total composition. Solid salts such as sodium bicarbonate, sodium chloride, potassium bicarbonate or potassium chloride may totally or partially replace the polyol career.

Tableting lubricants, in minor amounts of about 0.1 to 5% by weight, may be incorporated into the tablet or lozenge formulation to facilitate the preparation of both the tablets and lozenges,. Suitable lubricants include vegetable oils such as coconut oil, magnesium stearate, aluminum stearate, talc, starch and carbowax.

Lozenge formulations contain about 2% gum as a barrier agent to provide a shiny surface as opposed to a tablet which has a smooth finish. Suitable non-cariogenic gums include Kappa carrageenan, carboxymethyl cellulose, hydroxyethyl cellulose, Gantrez, and the like.

The lozenge or tablet may optionally be coated with a coating material such as waxes, shellac, carboxymethyl cellulose, polyethylene/maleic anhydride copolymer or Kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following examples are further illustrative of the nature of the present invention, but it is understood that the invention is not limited thereto. All amounts and proportions referred to herein and in the appended claims are percent by weight.

EXAMPLE 1

The efficacy of N-methylpyrrolidone solutions to inhibit bacterial plaque formation in vitro was assessed using the chemostat plaque model as described in Gaffar et al., *Am. J. Dent.*, Vol. 3, Special Issue p. S7 (Sept. 1990). The experimental apparatus includes a chemostat (Bioflo, Model C32), a source of supplementing growth media, a mixing chamber and several flow cells. The flow cells were specifically designed to contain an experimental surface (hydroxyapatite disks 12 mm×1 mm thick) on which plaque formation was measured.

A mixed continuous culture of five species of oral microorganisms (*A. viscosus* LY7, *S. mutans* JBP, *S. sanguis* 34, *V. parvula* ATCC 17745, *F. nucleatum* 10953) was maintained in the chemostat according to conditions described by Bradshaw et al., "Effects of Carbohydrate Pulses and pH on Population Shifts with Oral Microbial Community In Vitro", *J. Dent. Res.* 9:1288–1302 (1989). Modified BM medium diluted five-fold with distilled water and supplemented with 2.5 g/l hog gastric mucin was used as the chemostat growth medium. The bacterial effluent from the chemostat (1 ml/minute) was combined with additional sterile modified BM media (1 ml/minute) containing 1 mM sucrose in a mixing chamber to achieve a total flow rate of 2 ml/minute. This mixture was then distributed to 2 flow cells, each with a flow rate of 1 ml/minute using a peristaltic pump. Bacterial plaque formation was measured after 48 hours. The flow cells were treated with a solution of 5% N-methylpyrrolidone for 30 seconds, twice daily. A total of four treatments were given during the 48 hour experimental period; at 2.5, 20, 26.5 and 44 hours after the start of the flow through the cell. After 48 hours the cells were rinsed with distilled water for 15 minutes at a flow rate of 1 ml/minute. The hydroxyapatite disks were then removed for analysis. The procedure was repeated except that the 5% N-methylpyrrolidone solution was replaced by deionized distilled water as a control.

At the completion of each experiment, approximately 5 hours after the last treatment, the flow cells were rinsed with distilled water for 15 minutes at a flow rate of 1 ml/minute. Bacterial plaque formed on hydroxyapatite disks was removed by immersing the disks in 2 ml of 0.1N NaOH in a shaking water bath at 37° C. for 45 minutes. After removing the disks, the samples were sonicated to disperse the plaque. Turbidity of the resulting solution was measured at 610 nm in a spectrophotometer. A 0.1 ml sample was assayed for protein quantity using the Pierce BCA assay kit (Pierce Rockford, Ill.) A 1 ml aliquot of the sample was used for the determination of DNA according to the method of Labarca et al., "A Simple, Rapid Sensitive DNA Assay Procedure", *Anal. Biochem.*, 102:344–352 (1980).

Analysis of the plaque film on germanium prisms was done using the method of attenuated total reflectance Fourier transform infrared spectroscopy (ATR/FT-IR). At completion of the experiment, the germanium prisms were air dried in a vertical position prior to analysis. A Perkin Elmer (Norwalk, Conn.), Model 1725 FT-Infrared Spectrometer was used for the ATR/FT-IR measurements. The prisms were scanned from 4000 to 750 cm$^{-1}$ at a scan rate of 0.2 cm$^{-1}$ and a resolution of 4 cm$^{-1}$. The intensity bands (amide 1 and 2 bands) at 1650 and 1548 cm$^{-1}$, reflecting mainly protein content, were used as an estimate of the quantity of bacterial plaque present. The results are shown in Table 2.

TABLE 2

| | Plaque Parameters (% Reduction vs. Placebo) | | | |
|---|---|---|---|---|
| | | Hydroxyapatite Disks | | |
| | OD[1] | Protein ug/ml | DNA ug/ml | Germanium Surface[2] |
| Water Placebo | — | — | — | — |
| 5% N-methylpyrrolidone | 59.6 | 28.8 | 29.7 | 29.6 |

[1]OD = optical density
[2]measured by ATR-FTIR (Attenuated Total Reflectance-Fourier Transform Infrared Spectroscopy)

As shown in Table 2, twice a day treatment with a 5% solution of N-methylpyrrolidone results in a substantial reduction in bacterial plaque formed on both hydroxyapatite and germanium surfaces as compared with the water control.

EXAMPLES 2–5

Aqueous solutions of N-methylpyrrolidone having the concentrations shown in Table 3 were tested on in vitro plaque formation using the Saliva Flow Cell System.

The Saliva Flow Cell System was operated in the following manner as described in part in Gaffar et al., *Amer. J. Dent.*, Vol.3, Special Issue, pp. S9–S10 (Sept, 1990). A 100 ml glass jar of saliva was provided with a rubber stopper, preperforated with two holes. A portion of a 1 ml Pyrex disposable pipette, inserted into each hole, served as connectors. Plastic tubing having an internal diameter of 3.17 mm, served as the "vein" of the flow system.

The flow system was set up in an incubator (Precision Model 4) at 37° C., with the flow cells in a vertical position to minimize air entrapment. Two peristaltic pumps (Model P3), supplied with pre-cut silicone tubing (3.1 mm internal diameter), were used to produce a steady and pulseless flow rate. Pump I was used to draw saliva from the dispenser through the flow cell and then back to the saliva reservoir for recirculation. Pump II was used to pulse the flow cell. Y-shaped connectors linked the two pumps. The flow from each pump was alternately shut off during recirculation and pulsing.

Whole human saliva, supplemented with 10% TSB (tryptic soy broth), was circulated through the flow system at a flow rate of 1 ml/minute, corresponding to a shear stress of about 0.32 dynes-cm$^{-2}$. Circulation was performed for up to 72 hours, with TSB-saliva changes every 24 hours.

To assess the effect of N-methylpyrrolidone solutions on plaque formation, at t=15 minutes, the flow cells were initially pulsed with test samples at a flow rate of 10 ml/minute for 1 minute. Test solution residuals were removed by rinsing with the excess saliva, diluted another two-fold. TSB-saliva circulation was resumed after rinsing. Flow cells were treated twice within a 24 hour period, with subsequent change to fresh TSB-saliva every 24 hours. Treatments were continued for 72 hours. The procedure was repeated except that the N-methylpyrrolidone solution was replaced by deionized distilled water as a control.

All treatments and saliva changes were performed without disassembling the system or allowing the plates to go dry. Also, unless otherwise stated, the flow rate was 1 ml/minute.

After 72 hours, the pump was stopped and the recirculating system was disconnected from the dispenser. The flow cell was rinsed with deionized distilled water (single pass through) for 15 minutes to remove loosely bound materials. Although the flow rates were the same for the deposition and rinse phases, the shear stress was slightly lower in the rinse phase. The flow system was then disassembled and the test plates were air dried in a vertical position before analysis.

The results are shown in Table 3.

After drying for about 1 hour, the plates were analyzed using ATR-infrared spectroscopy and ellipsometry, which gives the chemical composition of the plaque. The relative absorbance at 1540 cm$^{-1}$ was used to quantify the proteinaceous materials (bacteria) making up the plaque.

TABLE 3

| | % REDUCTION VS. WATER | |
|---|---|---|
| N-methylpyrrolidone | Plaque on Germanium Surface[1] | Plaque film Thickness[2] |
| 0 | — | — |
| 1% | 22.3 | ND[3] |
| 5% | 35.1 | 11.6 |
| 10% | 57.8 | 45.3 |
| 20% | 76.5 | 73.9 |

[1]measured by ATR-FTIR spectroscopy
[2]measured by ellipsometry
[3]ND = not determined As shown in Table 3, N-methylpyrrolidone significantly reduced the amount of plaque on the substrate as compared with water, in a concentration dependent manner.

EXAMPLE 6

A mouth rinse in accordance with the present invention was prepared having the composition shown in Table 4.

TABLE 4

| COMPONENT | AMOUNT (w/w) |
|---|---|
| Sodium Saccharin | 0.03 |
| Glycerine | 10.00 |
| Sodium Lauryl Sulfate | 0.25 |
| N-methylpyrrolidone | 10.00 |
| Triclosan | 0.03 |
| Flavoring oil | 0.22 |
| Water | QS to 100 |

The composition was tested for plaque inhibiting effect using the Saliva Flow Cell System described in connection with Examples 2–5. Two control compositions were tested in the same manner. The first control composition [Control (1)] was the same as shown in Table 4 except for omitting N-methylpyrrolidone.

The second control composition [Control (2)] was the same as shown in Table 4 except for omitting both N-methylpyrrolidone and Triclosan. The results are shown in Table 5.

TABLE 5

| COMPOSITION | PERCENT REDUCTION | |
|---|---|---|
| | PLAQUE ON GERMANIUM SURFACE[1] | PLAQUE FILM THICKNESS[2] |
| Example 6 | 59 | 45 |
| Control (1) | 48 | 35 |
| Control (2) | — | — |

[1]measured by ATR-FTIR spectroscopy
[2]measured by ellipsometry

As shown in Table 5, N-methylpyrrolidone in combination with Triclosan has a greater plaque inhibiting effect than Triclosan alone, or a composition containing neither N-methylpyrrolidone or Triclosan.

EXAMPLE 7

The effect of N-methylpyrrolidone on caries development was tested in the following manner. A 30% by weight aqueous solution of N-methylpyrrolidone (0.1 ml) was used to test rat caries as described in Schmid et al., "Cariostatic Effects of Monofluorophosphate in Solutions and Dentifrices in Rats", *J. Clin. Dent.* Vol. No.3 pp. 75–82 (1989). The rat carries assay employed wearling rats exposed over a three week period to a cariogenic challenge induced by a high sucrose diet and inoculation with acidogenic strains of oral bacteria. The rats were treated daily with the N-methylpyrrolidone solution or deionized distilled water as a control and dental caries was evaluated at the end of the three week test period. The results are shown in Table 6.

TABLE 6

| Treatment | Mean Plaque Extent[2] | Dentinal Fissure Lesions | | Smooth Surface Lesions |
|---|---|---|---|---|
| | | Initial | Advanced | |
| Water | 1.9 | 12.0 | 11.2 | 16.3 |
| N-methylpyrrolidone | 0.3[1] | 7.4[1] | 3.3[1] | 3.0[1] |

[1]Significantly different from Water control ($p < 0.05$).
[2]Rated on a scale of 0 to 4 with 0 indicating no plaque formation and 4 the highest level of plaque formation.

The test data indicates that treatment with a 5% N-methylpyrrolidone solution significantly reduced the amount of plaque formed and the number of dental fissures and smooth surface caries as compared with the water control.

EXAMPLE 8

The following mouth rinse composition was prepared in accordance with the present invention:

| INGREDIENTS | AMOUNT (w/w) |
|---|---|
| Sodium Saccharin | 0.03 |
| Ethanol (95%) | 10.00 |
| Propylene Glycol | 7.00 |
| Triclosan | 0.03 |
| N-methylpyrrolidone | 5.0 |
| Sodium Lauryl Sulfate | 0.25 |
| Tauranol WSHP (n-methyl-N-cocoyl taurine) | 0.2 |
| Gantrez S-96 | 1.92 |
| NaOH (50% soln.) | 0.12 |
| Sorbitol | 10.00 |
| Flavoring Oil | 0.145 |
| Water | QS to 100 |

The composition was prepared by combining the propylene glycol and ethanol. Triclosan and the flavoring oil were added to the glycol/ethanol mixture to form a first mixture. All of the remaining components of the mouth rinse composition were combined in water to form a second mixture. The first and second mixtures were then combined to form the mouth rinse composition.

EXAMPLE 9

The following dentifrice composition was prepared in accordance with the present invention:

| INGREDIENTS | AMOUNT (w/w) |
|---|---|
| Precipitated silica | 23.00 |
| Carboxymethylcellulose | 1.60 |
| N-methylpyrrolidone | 10.00 |
| Sorbitol (70%) | 38.00 |
| Gantrez S-96 | 2.50 |
| Triclosan | 2.50 |
| Sodium lauryl sulfate | 0.30 |
| Sodium saccharine | 0.20 |
| Water | QS to 100 |

EXAMPLE 10

The following dentifrice composition was prepared in accordance with the present invention:

| INGREDIENTS | AMOUNT (w/w) |
|---|---|
| Precipitated silica | 23.000 |
| Carboxymethylcellulose | 1.600 |
| N-methylpyrrolidone | 10.000 |
| Sorbitol (70%) | 38.000 |
| Gantrez S-96 | 2.500 |
| $Na_4P_2O_7$ | 2.000 |
| Sodium fluoride | 0.243 |
| Sodium lauryl sulfate | 1.500 |
| Sodium saccharine | 0.200 |
| Water | QS to 100 |

EXAMPLE 11

The following mouth rinse composition was prepared in accordance with the present invention.

| INGREDIENTS | AMOUNT (w/w) |
|---|---|
| Ethanol | 10.00 |
| N-methylpyrrolidone | 5.00 |
| PEG-40 Sorbitan diisostearate | 0.20 |
| Chlorhexidine digluconate | 0.12 |
| Sodium saccharine | 0.03 |
| Glycerine | 10.00 |
| Flavoring Oil | 0.14 |
| Deionized Water | QS to 100 |

EXAMPLE 12

The following mouth rinse composition was prepared in accordance with the present invention.

| INGREDIENTS | AMOUNT (w/w) |
|---|---|
| Ethanol | 10.00 |
| N-methylpyrrolidone | 5.00 |
| PEG-40 Sorbitan diisostearate | 0.20 |
| Cetylpyridinium chloride | 0.12 |
| Sodium saccharine | 0.03 |
| Glycerine | 10.00 |
| Flavoring Oil | 0.14 |
| Deionized Water | QS to 100 |

This invention has been described with respect to preferred embodiments and it will be understood that modifications and variations thereof obvious to those skilled in the art are to be included within the spirit and purview of this application and the scope of the appended claims.

What we claim is:

1. An oral composition comprising a liquid vehicle suitable for topically contacting dental surfaces and gums, an anticalculus agent and as an antiplaque agent, about 0.5 to 20% by weight based on the total weight of the composition of N-methylpyrrolidone as an antiplaque agent.

2. The oral composition of claim 1 comprising about 1 to 15% by weight of N-methylpyrrolidone.

3. The oral composition of claim 2, wherein N-methylpyrrolidone is present in amount of about 5 to 10% by weight.

4. The oral composition of claim 1 wherein an anticalculus agent is present and said anticalculus agent is a linear molecularly dehydrated polyphosphate.

5. The oral composition of claim 4, wherein the amount of the anticalculus agent is about 0.1 to 7.0% by weight based on the total weight of the composition.

6. The oral composition of claim 4 wherein the linear molecularly dehydrated polyphosphate is selected from tetraalkali metal pyrophosphates.

7. The oral composition of claim 4 further comprising an enzyme inhibiting effective mount of a synthetic anionic polymeric polycarboxylate.

8. The oral composition of claim 7 wherein the synthetic anionic polymeric polycarboxylate is present in an amount of about 0.05 to 3% by weight.

9. The oral composition of claim 4 further comprising a source of fluoride ions in an amount of about 0.005 to 3.0% by weight.

10. The oral composition of claim 4 further comprising an effective amount of a cationic antibacterial agent.

11. The oral composition of claim 10 wherein the amount of the cationic antibacterial agent is about 0.001 to 15% by weight.

12. A method for reducing plaque and calculus formation comprising topically contacting dental surfaces and gums with an oral composition of claim 4.

13. The oral composition of claim 6 wherein said polyphosphate comprise tetrasodium or tetrapotassium pyrophosphate or a mixture thereof.

14. The oral composition of claim 8 wherein said polycarboxylate comprises a copolymer of vinyl methyl ether with maleic anhydride or acid.

15. The oral composition of claim 9 wherein said source of fluoride ions comprises sodium fluoride or sodium monofluorophosphate or a mixture thereof.

16. The oral composition of claim 15 further containing about 0.05 to 3% of a synthetic anionic polymeric polycarboxylate.

17. The oral composite of claim 11 wherein said cationic antibacterial agent comprises chlorhexidine digluconate or cetyl pyridinium chloride.

18. The oral composition of claim 17 further containing 0.05 to 3% of a synthetic anionic polymeric polycarboxylate and 0.005 to 3% of a source of fluoride ions.

19. The oral composition of claim 10 further containing about 0.005% to 4% of a water soluble or swellable antibacterial enhancing agent which contains at least one delivery-enhancing functional group which enhances delivery of said antibacterial agent to oral tooth and gum surfaces and at least one retention enhancing group which enhances attachment or bonding of said antibacterial agent to oral tooth and gum surfaces.

20. A method for reducing plaque and calculus formation comprising topically contacting dental surfaces and gums with the composition of claim 8.

21. A method for reducing plaque and calculus formation comprising topically contacting dental surfaces and gums with the composition of claim 9.

22. A method for reducing plaque and calculus formation comprising topically contacting dental surfaces and gums with the composition of claim 11.

* * * * *